United States Patent
Hefner, Jr.

(10) Patent No.: US 8,519,066 B2
(45) Date of Patent: Aug. 27, 2013

(54) POLY(ALLYL ETHERS) OF POLYCYCLOPENTADIENE POLYPHENOL

(75) Inventor: Robert E. Hefner, Jr., Rosharon, TX (US)

(73) Assignee: Dow Global Technologies LLC, Midland, MI (US)

( * ) Notice: Subject to any disclaimer, the term of this patent is extended or adjusted under 35 U.S.C. 154(b) by 59 days.

(21) Appl. No.: 13/643,863

(22) PCT Filed: Apr. 21, 2011

(86) PCT No.: PCT/US2011/000711
§ 371 (c)(1), (2), (4) Date: Oct. 26, 2012

(87) PCT Pub. No.: WO2011/136847
PCT Pub. Date: Nov. 3, 2011

(65) Prior Publication Data
US 2013/0041114 A1    Feb. 14, 2013

Related U.S. Application Data

(60) Provisional application No. 61/329,385, filed on Apr. 29, 2010.

(51) Int. Cl.
  C08G 8/30    (2006.01)
  C08F 283/00  (2006.01)

(52) U.S. Cl.
  USPC .................................................. 525/502

(58) Field of Classification Search
  USPC .................................................. 525/502
  See application file for complete search history.

(56) References Cited

U.S. PATENT DOCUMENTS

| | | | |
|---|---|---|---|
| 3,419,624 A | | 12/1968 | Cotter et al. |
| 3,450,746 A | * | 6/1969 | Stapfer ............... 560/57 |
| 3,625,874 A | * | 12/1971 | Cottman et al. .......... 525/149 |
| 4,456,129 A | | 6/1984 | Baber |
| 4,540,829 A | | 9/1985 | Hefner, Jr. |
| 4,546,131 A | | 10/1985 | Hefner, Jr. |
| 4,611,022 A | | 9/1986 | Hefner, Jr. |
| 4,629,762 A | | 12/1986 | Hefner, Jr. |
| 4,629,763 A | | 12/1986 | Hefner, Jr. |
| 4,629,764 A | | 12/1986 | Hefner, Jr. |
| 4,661,553 A | | 4/1987 | Hefner, Jr. |
| 4,707,533 A | | 11/1987 | Hefner, Jr. |
| 4,728,708 A | * | 3/1988 | Zupancic et al. .......... 526/293 |
| 4,766,184 A | | 8/1988 | Hefner, Jr. |
| 4,782,124 A | | 11/1988 | Hefner, Jr. et al. |
| 4,786,700 A | * | 11/1988 | Zupancic et al. .......... 526/292.9 |
| 4,820,740 A | * | 4/1989 | Li ............... 521/32 |
| 4,871,831 A | * | 10/1989 | Zweig et al. ............... 528/205 |
| 4,908,096 A | * | 3/1990 | Zupancic ............... 216/49 |
| 4,945,138 A | * | 7/1990 | Hefner et al. .............. 525/502 |
| 5,077,380 A | | 12/1991 | Hefner, Jr. et al. |
| 5,159,030 A | | 10/1992 | Hefner, Jr. |
| 5,191,128 A | * | 3/1993 | Li ............... 568/720 |

(Continued)

FOREIGN PATENT DOCUMENTS

| EP | 0315089 | 5/1989 |
|---|---|---|
| GB | 1009019 | 11/1965 |

(Continued)

OTHER PUBLICATIONS

International Search Report and Written Opinion from related PCT application PCT/US2011/000711 dated Jul. 19, 2011, 13 pages.

(Continued)

Primary Examiner — Mike M Dollinger
(74) Attorney, Agent, or Firm — Brooks, Cameron & Huebsch, PLLC

(57) ABSTRACT

Embodiments include poly(allyl ether)s of polycyclopentadiene polyphenol that can be obtained by allylation of a polycyclopentadiene polyphenol, where the aromatic hydroxyl group(s) (—OH) are converted to $HR^1C=CR^1-CH_2-O-$ and/or $H_2R^1C-CR^1=HC-O-$, where $R^1$ is as described herein. Embodiments also include thermosettable compositions including the poly(allyl ether)s of polycyclopentadiene polyphenol and products obtained by curing the thermosettable compositions.

15 Claims, No Drawings

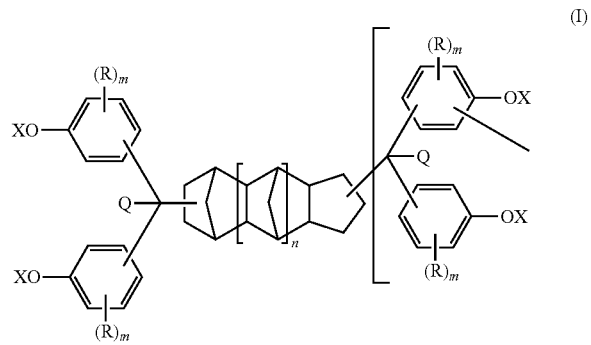

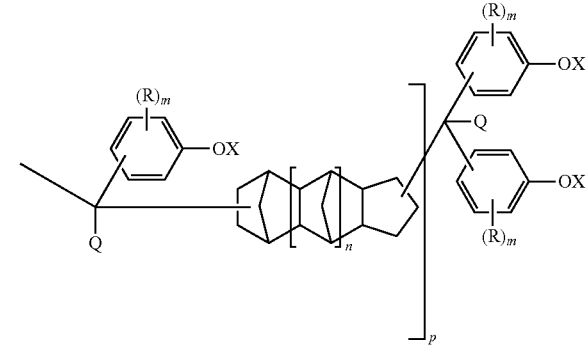

(56) References Cited

U.S. PATENT DOCUMENTS

| | | |
|---|---|---|
| 5,206,321 A | 4/1993 | Hefner, Jr. et al. |
| 5,281,675 A | 1/1994 | Hefner, Jr. et al. |
| 5,428,125 A | 6/1995 | Hefner, Jr. et al. |
| 5,442,039 A | 8/1995 | Hefner, Jr. et al. |
| 5,602,211 A | 2/1997 | Hefner, Jr. et al. |
| 6,307,108 B1 | 10/2001 | Argyropoulos et al. |
| 7,321,068 B2 | 1/2008 | Papp et al. |
| 2010/0189706 A1 | 7/2010 | Chang et al. |
| 2011/0009559 A1 | 1/2011 | Mullins et al. |
| 2011/0009560 A1 | 1/2011 | Hefner, Jr. et al. |
| 2011/0009562 A1 | 1/2011 | Mullins et al. |
| 2011/0040046 A1 | 2/2011 | Hefner, Jr. et al. |
| 2011/0046321 A1 | 2/2011 | Earls et al. |
| 2012/0238668 A1 | 9/2012 | Metral et al. |
| 2012/0238709 A1 | 9/2012 | Metral et al. |
| 2012/0289663 A1 | 11/2012 | Mullins et al. |

FOREIGN PATENT DOCUMENTS

| | | |
|---|---|---|
| WO | 8905318 | 6/1989 |
| WO | 2009114465 | 9/2009 |
| WO | 2009114466 | 9/2009 |

OTHER PUBLICATIONS

International Preliminary Report on Patentability from related PCT application PCT/US2011/000711 dated Jul. 2, 2012, 15 pages.
Green, et al. "Protective Groups in Organic Synthesis", Wiley-Interscience, New York, 1999, 67-74, 708-711.
Krompiec, et al. "Isomerization of allyl aryl ethers to their 1-propenyl derivatives catalysed by ruthenium complexes" Journal of Molecular Catalysis A: Chemical vol. 219, issue 1, 2004, 29-40.
Longoni, et al., "Hydroformylation and hydrocarbonylation of dicyclopentadiene with cobalt—rhodium catalytic systems promoted by triphenylphosphine: Synthesis of monoformyltricyclodecenes, diformyltricyclodecanes and di(tricyclodecenyl)ketones", Journal of Molecular Catalysis 68, 1991, 7-21.
Encyclopedia of Polymer Science and Technology, "Plastics, Resins, Rubbers, Fibers", vol. 1, 1964, 750-807.
Kirk-Othmer, Encyclopedia of Chemical Technology, 5th edition, vol. 8, 2010, p. 219-235.
Kirk-Othmer, Encyclopedia of Chemical Technology, 5th edition, vol. 10, 2010, pp. 347-470.
Muthyala, et al. "Bridged bicyclic cores containing a 1,1-diarylethylene motif are high-affinity subtype-selective ligands for the estrogen receptor", American Chemical Society, Journal of Medicinal Chemistry (2003), 46(9), 1589-1602.
Lekishvili, et al. "Polymers with organic-inorganic chains for the light-valve projection", Soobshcheniya Akademii Nauk Gruzinskoi SSR (1980), 98(1), 85-88.
Mukherjee, et al., "Pharmacophore mapping of selective binding affinity of estrogen modulators through classical and space modeling approaches: exploration of bridged-cyclic compounds with diarylethylene linkage", Journal of Chemical Information and Modeling (2007), 47(2), 475-487.
H.E. Lee and K. Neville, "Handbook of Epoxy Resins", McGraw-Hill, New York, 1967, chapter 2, pp. 2-1 through 2-33.
Paquin, "Epoxidverbindungen und Epoxidharze", Springer-Verlag, Berlin, 1958, chapter 5, 131 pages.
Byrne, et al. "Magnesium-Oppenauer Oxidation of Alcohols to Aldehydes and Ketones", Tetrahedron Letters, vol. 28, No. 7, 1987, pp. 769-772.
Itsuno, et al. "Reaction of Aldehyde O-Alkyl Oxime with Organometallic Compounds", Tetrahedron Letters, vol. 27, No. 26, 1986, 3033-3036.
Hirao, et al. "Versatile Synthesis of ab-acetylenic ketones by oxidative nucleophilic addition of vanadium acetylides", Tetrahedron Letters, No. 27, No. 8, 1986, pp. 933 and 934.
Adlington, et al. "Azo Anions in Synthesis t-Butylhydrazones as Acyl-anion Equivalents", Journal of the Chemical Society: Chemical Communications, 1983, 1040-1041.
Martin and Bauer "Cyanic Acid Esters From Phenols: Phenyl Cyanate", Organic Synthesis, vol. 61, 1983, pp. 35-68.
Hwang, et al. "Dielectric behavior and properties of a cyanate ester containing dicyclopentadiene 1", Journal of Appiled Polymer Science, vol. 96, No. 6, 2005, pp. 2079-2089.

* cited by examiner

POLY(ALLYL ETHERS) OF POLYCYCLOPENTADIENE POLYPHENOL

This application is a National Stage application under 35 U.S.C. 371 of PCT/US2011/000711, filed on Apr. 21, 2011 and published as WO 2011/136847 A1 on Nov. 3, 2011, which claims the benefit of U.S. Provisional Application Ser. No. 61/329,385 filed Apr. 29, 2010, the entire contents of which are incorporated herein by reference in its entirety.

FIELD OF DISCLOSURE

This disclosure relates to thermosettable monomers, and in particular poly(allyl ether)s of polycyclopentadiene polyphenol.

BACKGROUND

Thermosettable monomers are compounds that can be crosslinked. Crosslinking, also referred to as curing, converts the thermosettable monomers, which have a relatively low molecular weight, into crosslinked polymers, which have a relatively high molecular weight, by chemical reaction. Some of these crosslinked polymers, which can be said to be thermoset, can soften when heated, but do not melt or flow.

Many types of thermosettable monomers and crosslinked polymers are available. Thermosettable monomers can be purchased as pellets, powders, granules, or liquids. Alternatively, thermosettable monomers that have undergone partial curing can be purchased in stock shapes such as bars, sheets, and films.

Thermosettable monomers and crosslinked polymers can be based on a variety of chemistries. Examples of these chemistries include epoxy resins, vinyl ester resins, polycyanates, polyacrylates, unsaturated polyesters, polymaleimides, polyureas, and polyurethanes.

Some properties of thermosettable monomers and crosslinked polymers that can be considered for particular applications include mechanical properties, thermal properties, electrical properties, optical properties, processing properties, and physical properties. Mechanical properties can include flexural strength, tear strength, tensile strength, yield strength, tensile modulus, elongation, and impact toughness. Thermal properties can include maximum use temperature, deflection temperature, glass transition temperature, thermal conductivity, and coefficient of thermal expansion. Electrical and optical properties can include electrical resistivity, dielectric strength, dielectric constant or relative permittivity, index of refraction, and light transmission. Processing and physical properties can include bulk or apparent density, water absorption, viscosity, process temperature, shrinkage, and melt flow index.

SUMMARY

For the various embodiments, the poly(allyl ether)s of polycyclopentadiene polyphenol are represented by the following Formula I:

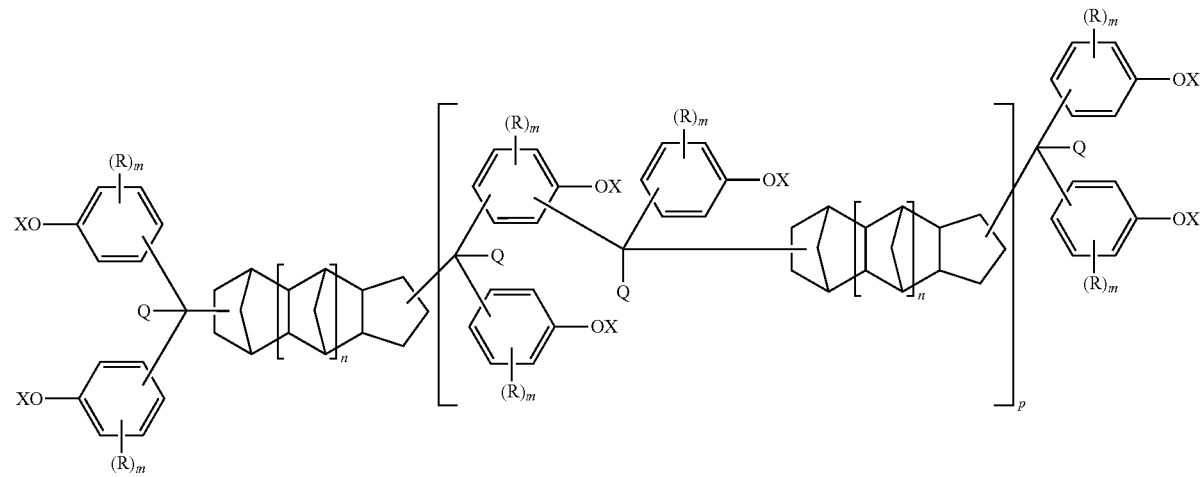

in which each n independently has a value from zero to 20; each m independently has a value of zero to 3; p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; each Q is independently hydrogen or an alkyl group containing 1 to 6 carbon atoms; and each X is independently selected from the group consisting of hydrogen, $HR^1C=CR^1-CH_2$, and $H_2R^1C-CR^1=HC$, where each $R^1$ is independently selected from the group consisting of hydrogen and alkyl groups having from 1 to 3 carbon atoms, with the proviso that when each X is hydrogen then at least one R group is selected from the group consisting of $HR^1C=CR^1-CH_2$ and $H_2R^1C-CR^1=HC$.

Embodiments of the present disclosure also include a thermosettable composition that includes the poly(allyl ether)s of polycyclopentadiene polyphenol represented by Formula I.

Embodiments of the present disclosure also include thermosettable compositions including a comonomer. Embodiments of the present disclosure also include products that are obtainable by curing the thermosettable compositions including the poly(allyl ether)s of polycyclopentadiene polyphenol represented by Formula I.

The above summary of the present disclosure is not intended to describe each disclosed embodiment or every implementation of the present disclosure. The description that follows more particularly exemplifies illustrative embodiments.

DETAILED DESCRIPTION

Embodiments of the present disclosure provide poly(allyl ether)s of polycyclopentadiene polyphenol. The poly(allyl ether)s of polycyclopentadiene polyphenol of the present disclosure can provide a high functionality, herein being at least four functional groups per molecule, which can help provide properties that are desirable for some applications. The term poly(allyl ether)s as used herein is also intended to encompass the poly(1-propenyl ether)s, that is, those compositions of Formula I wherein at least one of X and/or R is the $H_2R^1C—CR^1=HC$ group.

The poly(allyl ether)s of polycyclopentadiene polyphenol can be included in a thermosettable composition. Herein, a composition can be single-component or multi-component. For one or more embodiments, the thermosettable composition is cured to form a homopolymer. For one or more embodiments, the thermosettable composition is cured to form a copolymer. Thermosettable compositions that include the poly(allyl ether)s of polycyclopentadiene polyphenol can provide a relatively lower cure enthalpy, as compared some other thermosettable compositions, as seen in the Examples and Comparative Examples. This relatively lower cure enthalpy can help to control exothermic chemical reactions that occur during curing. Additionally, the relatively lower cure enthalpy can help prevent material decomposition, defect formation, and/or damage to manufacturing equipment that can occur with the relatively greater peak cure enthalpies. For one or more embodiments, the disclosed thermosettable compositions that include the poly(allyl ether)s of polycyclopentadiene polyphenol can provide improvements to a cure profile, for example, more rapid onset to uncatalyzed cure, as seen in the Examples and Comparative Examples.

For one or more embodiments, the disclosed thermosettable compositions that include the poly(allyl ether)s of polycyclopentadiene polyphenol can provide enhanced thermal stability, as compared some other thermosettable compositions, as seen in the Examples and Comparative Examples.

Products that are obtained by curing the thermosettable compositions disclosed herein can have a greater glass transition temperature as compared to products obtained by curing other compositions, as seen in the Examples.

For the various embodiments, the poly(allyl ether)s of polycyclopentadiene polyphenol are represented by the following Formula I:

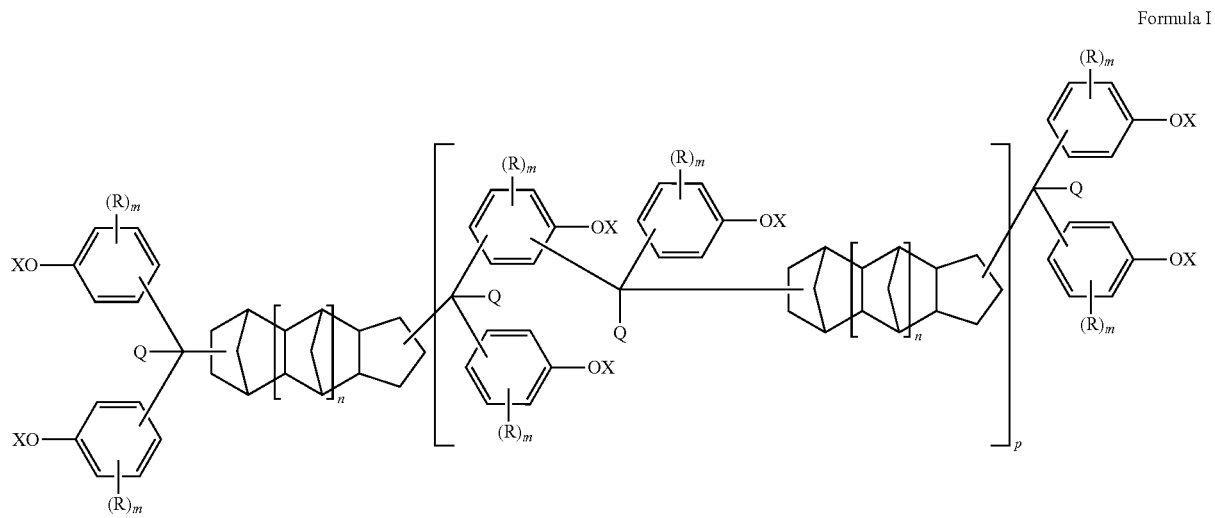

Formula I in which each n independently has a value from zero to 20; each m independently has a value of zero to 3; p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; each Q is independently hydrogen or an alkyl group containing 1 to 6 carbon atoms; and each X is independently selected from the group consisting of hydrogen, $HR^1C=CR^1—CH_2$, and $H_2R^1C—CR^1=HC$, where each $R^1$ is independently selected from the group consisting of hydrogen and alkyl groups having from 1 to 3 carbon atoms, with the proviso that when each X is hydrogen then at least one R group is selected from the group consisting of $HR^1C=CR^1—CH_2$ and $H_2R^1C—CR^1=HC$.

As discussed herein, each n can independently have a value from zero to 20. Preferably, each n can independently have a value from zero to 3, and most preferably each n can independently have a value from zero to 2. Preferably each m independently has a value of zero or 1. Preferably, p has a value from zero to 5, more preferably p has a value from zero to 2, and most preferably p has a value from zero to 1.

The terms "alkyl" and "alkenyl" as used herein include the corresponding cycloaliphatic groups such as, e.g., cyclopentyl, cyclohexyl, cyclopentenyl, and cyclohexenyl. Where two alkyl and/or alkenyl groups are attached to two carbon atoms of an aliphatic or aromatic ring, they may be combined to form an alkylene or alkenylene group which together with the carbon atoms to which this group is attached can result in a ring structure, preferably being 5 or 6 membered.

For one or more embodiments, the alkyl group(s) and/or the alkyloxy group(s) can include from 1 to 4 carbon atoms, and in some preferred embodiments, 1 or 2 carbon atoms. Examples of these groups include, but are not limited to, methyl, ethyl, propyl, isopropyl, n-butyl, isobutyl, sec-butyl, tert-butyl, methoxy, ethoxy, propoxy, isopropoxy, n-butoxy, isobutoxy, sec-butoxy, and tert-butoxy. The alkyl and alkoxy groups may be substituted with one or more (e.g., 1, 2, or 3) substituents. If more than one substituent is present, the substituents may be the same or different. Examples of the substituents include, but are not limited to, halogen atoms such as, F, Cl, and Br. Examples substituted alkyl and/or alkoxy groups include, but are not limited to, $CF_3$, $CF_3CH_2$, $CCl_3$, $CCl_3CH_2$, $CHCl_2$, $CH_2Cl$, $CH_2Br$, $CCl_3O$, $CHCl_2O$, $CH_2ClO$, and $CH_2BrO$.

For one or more embodiments, the alkenyl group(s) and/or the alkenyloxy group(s) can include 3 or 4 carbon atoms and, in some preferred embodiments, 3 carbon atoms. Examples of these groups include, but are not limited to, allyl, methallyl, and 1-propenyl. The alkenyl and alkenyloxy groups may be substituted with one or more (e.g., 1, 2, or 3) substituents. If more than one substituent is present, the substituents may be the same or different. Examples of the substituents include, but are not limited to, halogen atoms such as, F, Cl, and Br.

As discussed herein, each Q is independently hydrogen or an alkyl group containing 1 to 6 carbon atoms. For one or more embodiments each Q is hydrogen. The alkyl group(s) can include from 1 to 4 carbon atoms and, for some preferred embodiments, 1 or 2 carbon atoms. Examples of these groups include, but are not limited to, methyl, ethyl, propyl, isopropyl, n-butyl, isobutyl, sec-butyl, tert-butyl. The alkyl groups may be substituted with one or more (e.g., 1, 2, or 3) substituents. If more than one substituent is present, the substituents may be the same or different. Examples of the substituents include, but are not limited to, halogen atoms such as, F, Cl, and Br. Examples of substituted alkyl groups include, but are not limited to, $CF_3$, $CF_3CH_2$, $CF_3CF_2$, $CCl_3$, $CCl_3CH_2$, $CHCl_2$, $CH_2Cl$, $CH_2Br$, and $CH_2CHBrCH_2Br$.

As discussed herein, each X is independently selected from the group consisting of hydrogen, $HR^1C=CR^1—CH_2$, and $H_2R^1C—CR^1=HC$, where each $R^1$ is independently selected from the group consisting of hydrogen and alkyl groups having from 1 to 3 carbon atoms. The alkyl group can be unsubstituted or substituted. For one or more embodiments it is preferred that X is unsubstituted. For one or more embodiments it is preferred that each X is the same. For one or more embodiments X is preferably allyl. Examples of the alkyl group include, but are not limited to, methyl, ethyl, propyl, and isopropyl. For one or more embodiments, methyl is preferred. For one or more embodiments X is preferably methallyl. The alkyl groups may be substituted with one or more (e.g., 1, 2, or 3) substituents. If more than one substituent is present, the substituents may be the same or different. Examples of the substituents include, but are not limited to, halogen atoms such as, F, Cl, and Br.

The disclosed poly(allyl ether)s of polycyclopentadiene polyphenol can be obtained by allylation of a polycyclopentadiene polyphenol, where the aromatic hydroxyl group(s) (—OH) are converted to $HR^1C=CR^1—CH_2—O—$ and/or $H_2R^1C—CR^1=HC—O—$, where $R^1$ is as described herein.

As used herein, the prefix "poly" means that a compound has two or more of a particular moiety. "Compound" refers to a substance composed of atoms or ions of two or more elements in chemical combination. For example, a cyclopentadiene compound having two cyclopentadiene moieties (dicyclopentadiene) is a specific polycyclopentadiene. Examples of compounds represented by Formula I include, but are not limited to, a poly(allyl ether) of a dicyclopentadiene polyphenol (novolac) prepared from condensation of dicyclopentadiene dialdehyde with phenol; a poly(methallyl ether) of a dicyclopentadiene polyphenol (novolac) prepared from condensation of dicyclopentadiene dialdehyde with phenol; a poly(allyl ether) of a dicyclopentadiene polyphenol (novolac) prepared from condensation of dicyclopentadiene dialdehyde with 2-methylphenol; a poly(methallyl ether) of a dicyclopentadiene polyphenol (novolac) prepared from condensation of dicyclopentadiene dialdehyde with 2-methylphenol; a poly(allyl ether) of a dicyclopentadiene polyphenol (novolac) prepared from condensation of dicyclopentadiene dialdehyde with 2,6-dimethylphenol; a poly(methallyl ether) of a dicyclopentadiene polyphenol (novolac) prepared from condensation of dicyclopentadiene dialdehyde with 2,6-dimethylphenol; a poly(allyl ether) of a tricyclopentadiene polyphenol (novolac) prepared from condensation of tricyclopentadiene dialdehyde with phenol; a poly(methallyl ether) of a tricyclopentadiene polyphenol (novolac) prepared from condensation of tricyclopentadiene dialdehyde with phenol; a poly(allyl ether) of a dicyclopentadiene tetraphenol prepared from condensation of dicyclopentadiene dialdehyde with phenol; a poly(methallyl ether) of a dicyclopentadiene tetraphenol prepared from condensation of dicyclopentadiene dialdehyde with phenol; partial or complete Claisen rearrangement products of the poly(allyl ether) of a dicyclopentadiene polyphenol (novolac) prepared from condensation of dicyclopentadiene dialdehyde with phenol; and partial or complete Claisen rearrangement products of the poly(allyl ether) of a dicyclopentadiene tetraphenol prepared from condensation of dicyclopentadiene dialdehyde with phenol.

Monomers which carry at least one ortho-substituent on at least one aromatic ring may be used to block a Claisen rearrangement. A preferred example of such monomers of Formula I is the poly(allyl ether) of a dicyclopentadiene polyphenol (novolac) prepared from condensation of dicyclopentadiene dialdehyde with 2,6-dimethylphenol.

Further non-limiting examples of the monomers of Formula I include partial or complete Claisen rearrangement products of compounds of Formula I wherein at least one of the X groups is $HR^1C=CR^1—CH_2—$ or $H_2R^1C—CR^1=HC—$, where $R^1$ is as described herein. As a representative example, in the case of the tetra(allyl ether) of the dicyclopentadiene tetraphenol prepared from condensation of dicyclopentadiene dialdehyde with phenol, such Claisen rearrangement products may include, as a partial listing, compounds of Formulae (A)-(P), where X is $H_2C=CH—CH_2—$.

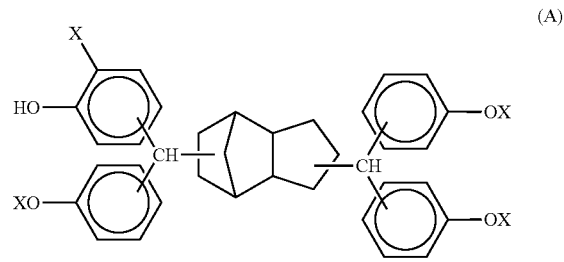

(A)

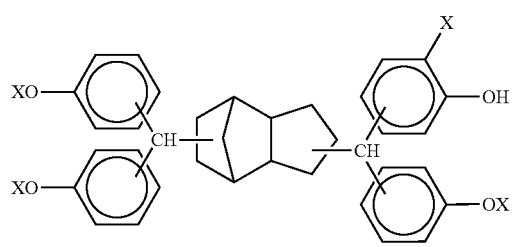
(B)
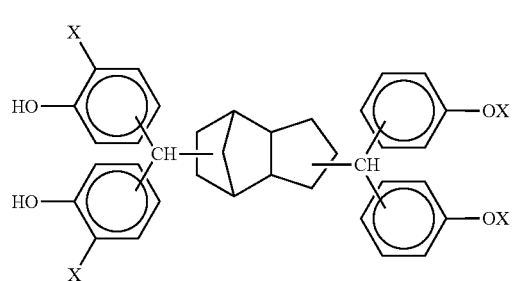
(C)
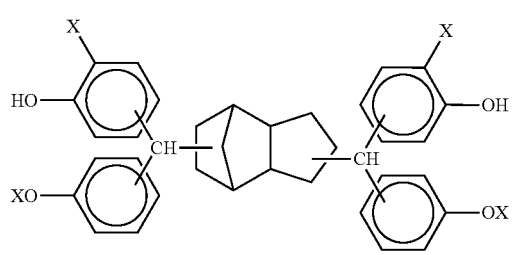
(D)
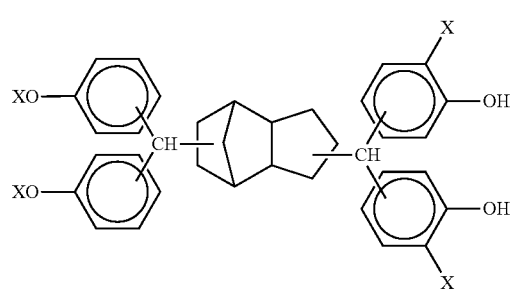
(E)
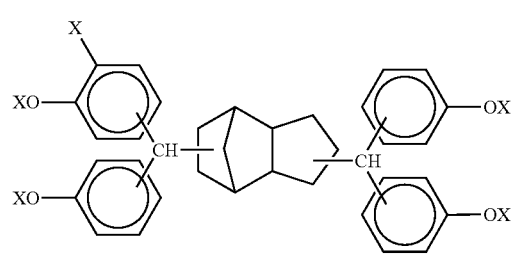
(F)
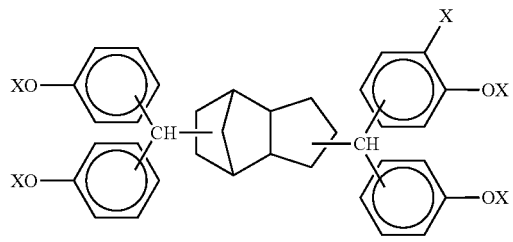
(G)
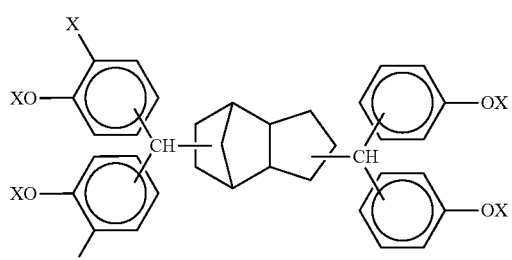
(H)
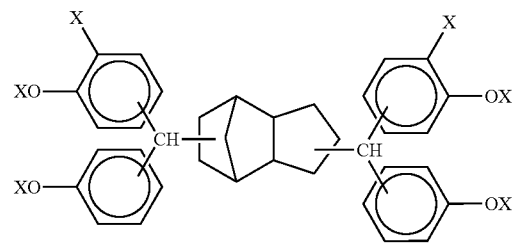
(I)
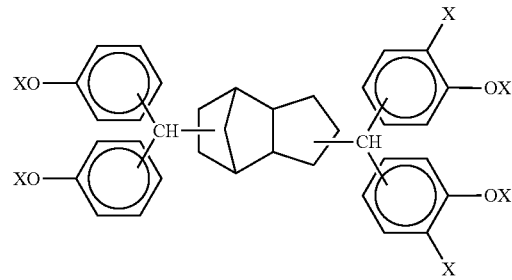
(J)
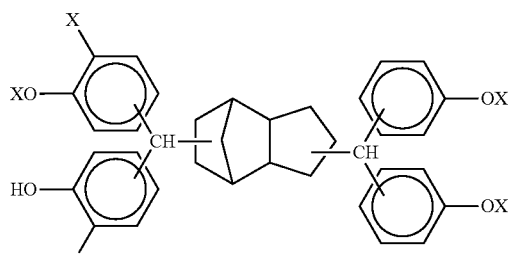
(K)
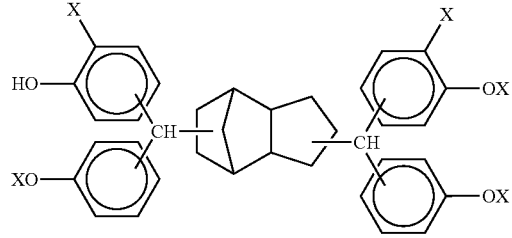
(L)
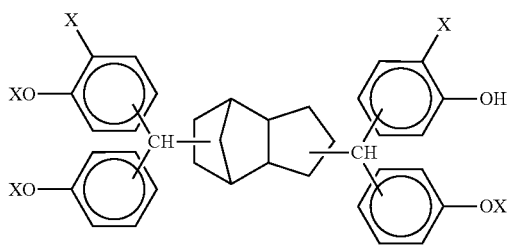
(M)

-continued

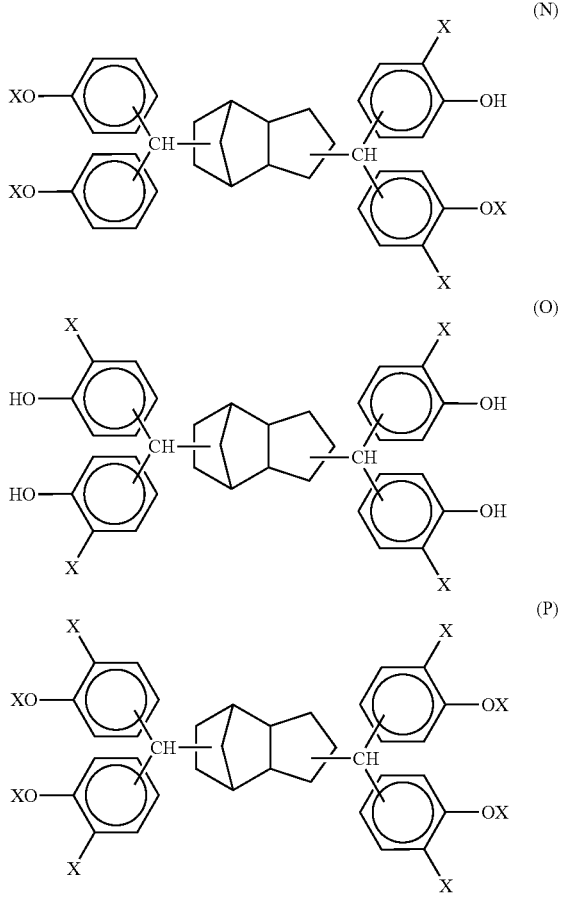

Further non-limiting examples of the above monomers of Formula I include monomers which carry at least one substituent on at least one aromatic ring to block a Claisen rearrangement. A representative example of such monomers is represented by Formula (Q), where X is $H_2C=CH-CH_2-$.

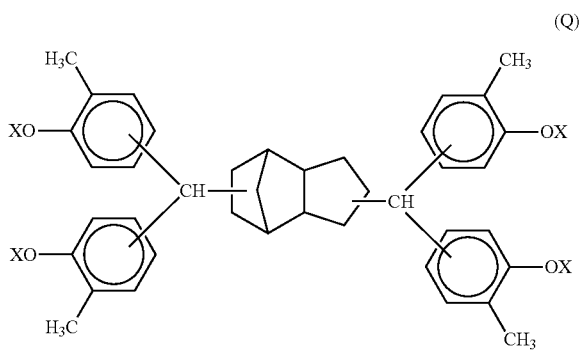

Polycyclopentadiene polyphenols can be produced from polycyclopentadiene dialdehydes. Polycyclopentadiene dialdehydes can be produced via hydroformylation of polycyclopentadiene, such as, dicyclopentadiene using syngas, a phosphine ligand, and a transition metal (from Groups 3 through 10) catalyst using a method such as described by G. Longoni, et al, J. of Molecular Catalysis 68, 7-21 (1991) or more generally in Kirk-Othmer, ENCYCLOPEDIA OF CHEMICAL TECHNOLOGY, Fifth Edition, Vol. 10, pp. 347-470 (2010). There can be variations in this process. For example, a method as described in U.S. Pat. No. 6,307,108 uses mixed polar/nonpolar solvents to ease the problem of catalyst recycle and product separation. The resulting polycyclopentadiene dialdehydes can then be condensed with phenols to form polycyclopentadiene polyphenols. Polycyclopentadiene can be prepared by heating cyclopentadiene to temperatures above 100° C. as disclosed by Kirk-Othmer, ENCYCLOPEDIA OF CHEMICAL TECHNOLOGY, Fifth Edition, Vol. 8, p. 223 (2010). All of the aforementioned references are incorporated herein in their entirety by reference.

The hydroformylation can occur at a pressure of 1 to 250 atmospheres and a temperature of 20° C. to 250° C. The syngas can include varying amounts of carbon monoxide and hydrogen. The syngas can include one or more inert gases, such as nitrogen.

The hydroformylation can be conducted using a rhodium catalyst without a ligand and at a syngas pressure of 200 to 350 atmospheres as discussed in U.S. Pat. No. 7,321,068. Examples of suitable ligands include, but are not limited to, carbon monoxide and organophosphine ligands having the general formula $PR^1R^2R^3$ where each $R^1$, $R^2$, and $R^3$ is a substituted or unsubstituted alkyl group, an aryl, an aralkyl, an alkaryl, a halide, or a combination thereof. A specific example includes, but is not limited to, n-butyldiphenylphosphine. An example of a suitable catalyst includes, but is not limited to, $Rh(CO)_2$(acetylacetonate).

During the hydroformylation amounts, such as 5 to 25 weight (wt.) percent (%) or less of the total reaction products, of polycyclopentadiene monoaldehydes, having varying degrees of saturation, may also be produced along with the polycyclopentadiene dialdehydes. An example of these polycyclopentadiene monoaldehydes is represented by the following Formula II, where n is as described herein:

Formula II $$\underset{HC}{\overset{O}{\|}}{-}\left[\text{tricyclic}\right]_n$$

The polycyclopentadiene monoaldehydes can be separated from the polycyclopentadiene dialdehydes. For example, a distillation process can be used to separate the polycyclopentadiene monoaldehydes from the polycyclopentadiene dialdehydes. However, using a mixture of the polycyclopentadiene monoaldehydes and the polycyclopentadiene dialdehydes can help control a level of functionality. For example, whereas novolac chemistry can be used to form the polycyclopentadiene polyphenols from the polycyclopentadiene dialdehydes, novolac chemistry can also be used to form polycyclopentadiene diphenols from the polycyclopentadiene monoaldehydes. An example of the polycyclopentadiene diphenols having a saturated cyclopentane ring is represented by the following Formula III:

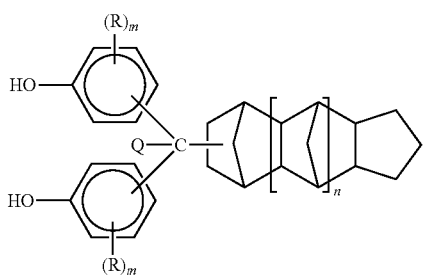

Formula III where n, m, R and Q are as described herein. Oligomers may also be present in the polycyclopentadiene diphenols. Thus, mixtures of polycyclopentadiene diphenols and polycyclopentadiene polyphenols may be produced.

The hydroformylation can produce isomeric ketones as described by Longoni. These ketones can be the predominant products when the hydrogen/carbon monoxide pressure is low (~1 atm). If these ketones are present in the product mix they can be condensed with phenol to form polyphenols of Formula IV, where n, m, and R are as described herein.

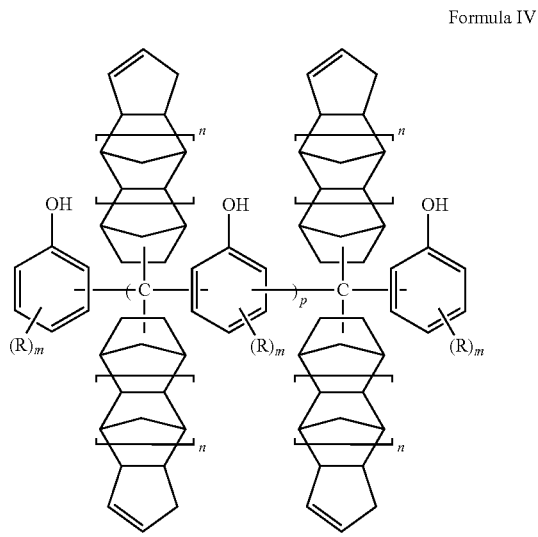

Formula IV

Using mixtures of the polycyclopentadiene monoaldehydes, polycyclopentadiene dialdehydes, and ketones may help control the level of functionality in a given thermosettable composition. For example, crosslink density for a thermosettable composition of the present disclosure can be adjusted (e.g., decreased or increased) based on the relative amounts of the polycyclopentadiene polyphenols and the polycyclopentadiene diphenols used in preparing the poly(allyl ether)s of dicyclopentadiene polyphenol. Adjusting the level of functionality in this way can allow for the properties, such as glass transition temperature (Tg), of the products obtained by curing the thermosettable compositions to be tailored to desired levels and/or balance with other properties, such as toughness, of the product.

Moreover, it may be possible to control the amount of dicyclopentadiene and/or polycyclopentadiene moieties in the polycyclopentadiene dialdehydes. The dicyclopentadiene and/or polycyclopentadiene can be formed through Diels-Alder chemistry using cyclopentadiene where, as discussed herein, the average value for n can be from zero to 20. So, for example, when the polycyclopentadiene moieties in the polycyclopentadiene dialdehydes are oligomers they can have a distribution of n values that is on average from 2 to 5. For other applications, n can have a value of zero or 1. The ability to control the dicyclopentadiene and/or polycyclopentadiene moieties in the polycyclopentadiene dialdehydes may also allow for the ability to control and/or tailor a crosslink density of a thermosettable composition while retaining some properties of the cured product.

The resulting polycyclopentadiene dialdehydes along with any of the polycyclopentadiene monoaldehydes and ketones can then undergo a novolac reaction to form polycyclopentadiene polyphenols. The novolac reaction involves the use of a phenol and an acid catalyst. For example, the polycyclopentadiene dialdehydes and molten phenol can be reacted at a temperature of 65° C. to 70° C. with stirring under a nitrogen atmosphere and in the presence of an acid catalyst. The resulting polycyclopentadiene dialdehydes, along with any of the polycyclopentadiene monoaldehydes, can then undergo a novolac reaction to form polycyclopentadiene polyphenols.

Polycyclopentadiene polyphenols can be prepared via a condensation reaction of a mole ratio of the polycyclopentadiene dialdehydes (and any polycyclopentadiene monoaldehydes) to phenol and/or substituted phenol, o-cresol, m-cresol, p-cresol, 2,4-dimethylphenol, 2,6-dimethylphenol, 1-naphthol, and 2-naphthol of 1:20 to 1:6, and preferably from 1:15 to 1:8; in the presence of an acid catalyst which is preferably from 0.1 to 2 wt. %, and more preferably from 0.1 to 1 wt. % based on the amount of phenol or substituted phenol compound employed. Higher mole ratios than 1:20 of the phenol or substituted phenol may be employed, however doing may require additional energy and thus expense to recover and recycle the excess phenol and/or substituted phenol.

Condensation reactions employing a large excess of the phenol and/or substituted phenol have been found to favor polycyclopentadiene polyphenols having a low polydispersity and weight average molecular weight. Likewise, as the amount of the phenol and/or substituted phenol is reduced, there can be an increase in oligomers of the polycyclopentadiene polyphenols, increasing the weight average molecular weight. Increased oligomer content favors higher hydroxyl functionality per molecule which may be highly beneficial for certain end uses but at the cost of higher viscosity. For some applications, very large excesses of phenol and/or substituted phenol may be employed; the molar ratio provided above can produce products rich in polycyclopentadiene polyphenol, and low in oligomers.

A solvent can be employed when forming the polycyclopentadiene polyphenols. With some phenols having relatively higher melt viscosities than some other phenols use of one or more solvents may be beneficial for maintaining a suitable reaction medium. The solvent can be inert to the reaction and/of the reaction products. The solvent may serve as an agent for the azeotropic removal of water from the condensation reaction. Examples of the solvent include, but are not limited to, toluene and xylene.

Suitable acid catalysts include, but are not limited to, protonic acids, such as hydrochloric acid, sulfuric acid, phosphoric acid; metal oxides, such as zinc oxide, aluminum oxide, magnesium oxide; organic acids, such as p-toluenesulfonic acid, oxalic acid, 3-mercapto-1-propane sulfonic acid, and combinations thereof 3-mercapto-1-propane sulfonic acid is a preferred acid catalyst or co-catalyst as it is highly selective in forming the polycyclopentadiene polyphenols and can eliminate a need for an azeotropic removal of water from the reaction products. The water can remain in the reactor, without quenching the novolac reaction.

Reaction temperatures and times vary, but can be from 5 minutes to 48 hours and reaction temperatures of from 20° C. to 175° C. may be employed. Preferably reaction temperatures and times can be from 15 minutes to 36 hours and reaction temperatures of from 30° C. to 125° C. Most preferably reaction temperatures and times can be from 30 minutes to 24 hours and reaction temperatures of from 35° C. to 75° C.

At the end of the reaction, the acidic catalyst can be removed by neutralization, for example by washing or extracting with water. Likewise, at the end of the reaction, excess phenol can be removed from the novolac product, for example, by distillation or extraction.

The polycyclopentadiene polyphenols can have a polydispersity index of less than 2. For example, the polydispersity index (the measure of distribution of molecular mass in a given polymer sample) of the polycyclopentadiene polyphenols can be from 1.3 to 1.4. These types of results indicate that both the n values and the p values of the polycyclopentadiene polyphenols are very uniform. Having a uniform chain length for the polycyclopentadiene polyphenols can allow for more desirable viscosity predictability in the viscosity of the thermosettable compositions of the present disclosure.

The polycyclopentadiene polyphenols can be represented by the following Formula V:

Allylmethyl carbonate can be prepared from a reaction of allyl alcohol and dimethyl carbonate. This reaction can provide a mixture of allylmethyl carbonate and diallyl carbonate. This mixture and/or pure allylmethyl carbonate can be employed in the transcarbonation reaction.

Allylation of the polycyclopentadiene polyphenol can be accomplished by a direct allylation reaction that can include a halide, an alkaline agent, and optionally a catalyst, such as a phase transfer catalyst. Examples of the halide include, but are not limited to, allyl halides and methallyl halides. Examples of allyl halides include, but are not limited to, allyl chloride and allyl bromide. Examples of methallyl halides include, but are not limited to, methallyl chloride and methallyl bromide. An example of the alkaline agent includes, but is not limited to, an aqueous solution of an alkali metal hydroxide. Examples of the alkali metal hydroxide include, but are not limited to, potassium hydroxide and sodium hydroxide. Examples of the catalyst include, but are not limited to, benzyltrialkylammonium halides and tetraalkylammonium halides. The allylation can include allylmethyl carbonate, diallyl carbonate, the halide, the alkaline agent, the catalyst, and combinations thereof along with the polycyclopentadiene polyphenol.

Direct allylation of the polycyclopentadiene polyphenol can occur at a temperature of 25° C. to 150° C. For some applications a temperature of 50° C. to 100° C. is preferred for Formula V

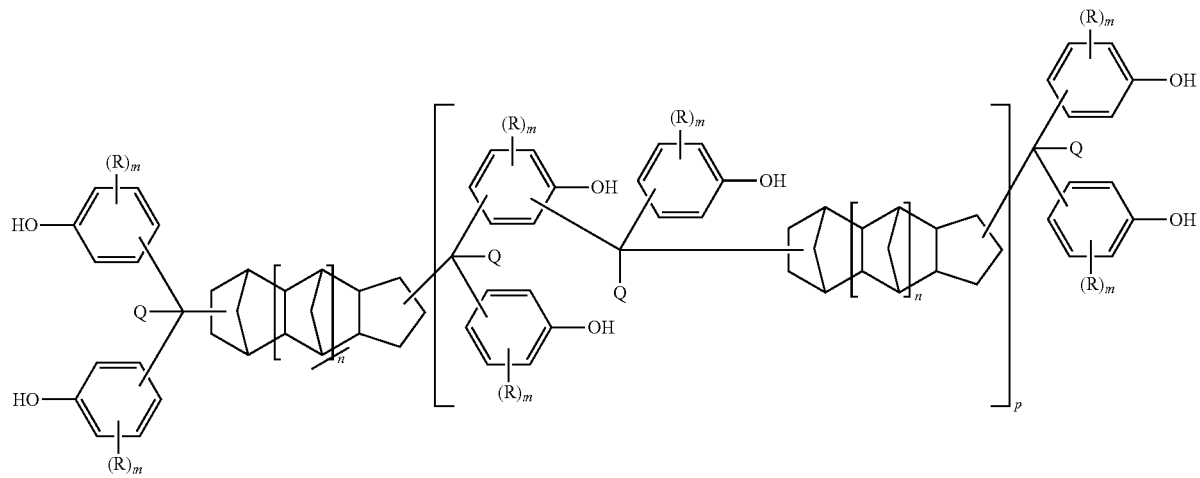

where n, m, p, R and Q are as described herein. Polycyclopentadiene polyphenols are discussed in U.S. Utility application Ser. No. 13/643,321, titled "POLYCYCLOPENTADIENE COMPOUNDS", The Dow Chemical Company docket number 68349, filed herewith, the disclosure which is incorporated herein by reference.

As discussed herein, the disclosed poly(allyl ether)s of polycyclopentadiene polyphenol can be obtained by allylation of the polycyclopentadiene polyphenol, where aromatic hydroxyl group(s) (—OH) are converted to $HR^1C=CR^1-CH_2-O-$ and/or $H_2R^1C-CR^1=HC-O-$, where $R^1$ is as described herein.

Allylation of the polycyclopentadiene polyphenol can be accomplished via a transcarbonation reaction. The transcarbonation reaction can include allylmethyl carbonate that is reacted with the polycyclopentadiene polyphenol in the presence of a catalytic amount of palladium on carbon and triphenylphosphine.

the allylation. Allylation of the polycyclopentadiene polyphenol can have a reaction time of 15 minutes to 8 hours. For some applications a reaction time of 2 hours to 6 hours is preferred. Allylation of the polycyclopentadiene polyphenol can include a solvent. An example of the solvent includes, but is not limited to, 1,4-dioxane.

In a direct allylation reaction, the allyl halide may be stoichiometrically reacted with the hydroxy groups of the polycyclopentadiene polyphenol. For various reaction conditions, variable amounts of a Claisen rearrangement product may be observed in this reaction, and can result in a mixture of O- and C-allylated products.

A reaction of a 1 to 1 mole ratio of the allyl halide with the hydroxy groups of the polycyclopentadiene polyphenol can provide an allylated bisphenol, wherein a major amount (about 80 or more percent) of the hydroxy groups of the polycyclopentadiene polyphenol have been converted to —O—CH$_2$—CH═CH$_2$ groups. Additionally, a minor amount (about 20 percent or less) of the allyl groups may have undergone thermally induced Claisen rearrangement and be present on the aromatic ring ortho and/or para to the hydroxy groups from which the rearrangement occurred. A reaction of less than a 1 to 1 mole ratio of allyl methyl carbonate in the transcarbonation reaction or of allyl halide in the direct allylation reaction with the hydroxy groups can provide partial allylation, with some free hydroxy groups remaining. Although the partially allylated compounds may be less preferred for some applications, they are within the scope of the present disclosure.

A preferred process uses a transcarbonation reaction wherein allylmethyl carbonate is stoichiometrically reacted with the polycyclopentadiene polyphenol to provide essentially total allylation of the hydroxy groups of the polycyclopentadiene polyphenol and provide the corresponding allylether (allyloxy) groups.

Isomerization of the allyloxy and allyl groups, if present, to the more reactive 1-propenyl groups may be performed in the presence of a base using the methods reported by T. W. Green and P. G. M. Wuts in Protective Groups in Organic Synthesis, Wiley-Interscience, New York, 67-74, 708-711 (1999) or in the presence of a catalytic amount of a ruthenium complex as described in Journal of Molecular Catalysis A: Chemical volume 219, issue 1, pages 29-40 (Sep. 1, 2004). Both of the aforementioned references are incorporated herein in their entirety.

The disclosed poly(allyl ether)s of polycyclopentadiene polyphenol can be included in a thermosettable composition. The thermosettable composition can be a solid phase, such as a powder, or a liquid phase, such as a solution, that includes the poly(allyl ether)s of polycyclopentadiene polyphenol. The poly(allyl ether)s of polycyclopentadiene polyphenol can have various n values and various p values, as described herein. For such mixtures the values of n and p can be described as number values for the average extent of oligomerization.

For one or more embodiments, the thermosettable composition is cured to form a product that is a homopolymer. A homopolymer is a polymer derived from one species of monomer. Herein the disclosed poly(allyl ether)s of polycyclopentadiene polyphenol are considered to be one species of monomer.

For one or more embodiments, the thermosettable composition is cured to form a product that is a copolymer. A copolymer is a polymer derived from two or more species of monomers. The two or more species of monomers can be referred to as comonomers. Herein one of the two or more species of monomers that is one of the comonomers is the disclosed poly(allyl ether)s of polycyclopentadiene polyphenol. For one or more embodiments a comonomer is selected from the group consisting polymaleimides, polycyanates, polycyanamides, epoxy compounds, allyl compounds, compounds containing one or more polymerizable ethylenically unsaturated group(s), and combinations thereof. As described herein, comonomers include prepolymers. Prepolymers are compounds, such as an oligomer or macromet, wherein the molecules of such are capable of entering, through reactive groups, into further polymerization. The prepolymers can be formed from the comonomers as described herein.

For one or more embodiments the thermosettable compositions including comonomers have a minimal active level of the poly(allyl ether)s of polycyclopentadiene polyphenol. This minimal active level can have different values depending upon the particular application. For example, an application where a lower cure enthalpy is desirable may have a different minimal active level of the poly(allyl ether)s of polycyclopentadiene polyphenol than another application where an increased glass transition temperature is desirable. For one or more embodiments the comonomer selected from the group consisting polymaleimides, polycyanates, polycyanamides, epoxy compounds, compounds containing one or more polymerizable ethylenically unsaturated group(s), and combinations thereof can be 5 weight percent to 90 weight percent of the monomers included in the thermosettable composition from which the copolymer is derived. Thus, for one or more embodiments the poly(allyl ether)s of polycyclopentadiene polyphenol are 10 weight percent to 95 weight percent of the monomers from which the copolymer is derived.

Herein, polymaleimides are compounds having two or more maleimide moieties. Examples of polymaleimides include, but are not limited to, 1,2-bismaleimido ethane; 1,4-bismaleimido butane; 1,6-bismaleimido hexane; 1,12-bismaleimido dodecane; 1,6-bismaleimido-(2,2,4-trimethyl) hexane; 1,3-bismaleimido benzene; 1,4-bismaleimido benzene; 4,4'-bismaleimido diphenyl methane; 4,4'-bismaleimido diphenyl ether; 4,4'-bismaleimido diphenyl sulfide; 4,4'-bismaleimido diphenyl sulfone; 4,4'-bismaleimido dicyclohexyl methane; 2,4-bismaleimido toluene; and 2,6-bismaleimido toluene.

Herein, polycyanates are compounds having two or more cyanate moieties. Examples of polycyanates include, but are not limited to, bisphenol A dicyanate, hexafluorobisphenol A dicyanate, tetramethylbisphenol F dicyanate, polycyanate of dicyclopentadiene polyphenol; 2-tert-butyl-1,4-dicyanatobenzene; 2,4,6-trimethyl-1,3-dicyanatobenzene; 4-chloro-1,3-dicyanatobenzene; 1,3,5-tricyanatobenzene; 4,4'-dicyanatodiphenyl; 2,2'-dicyanato-1,1'-binaphthyl; 4,4'-dicyanatodiphenyl ether; 3,3',5,5'-tetramethyl-4,4'-dicyanatodiphenyl ether; 3,3',5,5'-tetrachloro-4,4'-dicyanatodiphenyl ether; 4,4'-bis-[p-cyanatophenoxy]diphenyl ether; 4,4'-bis-[p-cyanatophenyl isopropyl]diphenyl ether; 4,4'-bis-[p-cyanatophenoxy]benzene; 4,4'-bis-[m-cyanatophenoxy]diphenyl ether; 4,4'-bis-[4-(4-cyanatophenoxy)phenyl sulphone]diphenyl ether; 4,4'-dicyanatodiphenyl sulphone; 3,3',5,5'-tetramethyl-4,4'-dicyanato diphenyl sulphone; 3,3',5,5'-tetrachloro-4,4'-dicyanatodiphenyl sulphone; 4,4'-bis-[p-cyanatophenyl isopropyl]diphenyl sulphone; 4,4'-bis-[(4-cyanato)-phenoxy]-diphenyl sulphone; 4,4'-bis-[(3-cyanato)-phenoxy] diphenyl sulphone; 4,4'-bis-[4-(4-cyanatophenyl isopropyl)-phenoxy]diphenyl sulphone; 4,4'-bis-[4-(4-cyanatophenyl sulphone)phenoxy]diphenyl sulphone; and 4,4'-bis-[4-(4-cyanato)diphenoxy]diphenyl sulphone.

Herein, polycyanamides are compounds having two or more cyanamide moieties. Examples of polycyanamides include, but are not limited to, the dicyanamides of 4,4'-diminodiphenylmethane; 4,4'-sulfonyldianiline; 4,4'-diaminodiphenyl oxide; 3,3'-dimethyl-4,4'-diaminobiphenyl; 4,4'-diaminostilbene; 4,4'-diaminophenyl benzoate; 4,4'-diamino-alpha-methylstilbene; tris(aminophenyl)methane; aniline-formaldehyde condensation products; the cyanamides of 4-amino-4'-hydroxybenzanilide; 4-amino-4'-hydroxystilbene; and p-aminophenol.

Examples of allyl compounds include, but are not limited to, allyl-s-triazines, allyl ethers, allyl esters, diethylene glycol bis(allylcarbonate)s, allyl phenols, and phosphorus containing allyl monomers. These allyl compounds, and other comonomers that can be included in the disclosed thermosettable compositions are described, for example, in the Encyclopedia of Polymer Science and Technology, volume 1, pages 750 to 807 (1964) published by John Wiley and Sons, Inc., the entire disclosure of which is expressly incorporated by reference herein. Some specific allyl monomers are triallyl isocyanurate; 2,4,6-tris(allyloxy)-s-triazine; hexaallylmelamine; hexa(allyloxymethyl)melamine; trimethylolpropane diallyl ether; 1,2,3-methallyloxypropane; o-diallyl bisphenol A; hexamethallyldipentaerythritol; diallyl phthalate; diallyl isophthalate; diethylene glycol bis(allylcarbonate); and allyl diphenyl phosphate.

An epoxy compound is a compound in which an oxygen atom is directly attached to two adjacent or non-adjacent carbon atoms of a carbon chain or ring system to form an epoxide or oxirane ring. The epoxy compound can be selected from the group consisting of aromatic epoxy compounds, alicyclic epoxy compounds, aliphatic epoxy compounds, and combinations thereof.

Examples of aromatic epoxy compounds include, but are not limited to, glycidyl ether compounds of polyphenols, such as hydroquinone, resorcinol, bisphenol A, bisphenol F, 4,4'-dihydroxybiphenyl, phenol novolac, cresol novolac, trisphenol (tris-(4-hydroxyphenyl)methane), 1,1,2,2-tetra(4-hydroxyphenyl)ethane, tetrabromobisphenol A, 2,2-bis(4-hydroxyphenyl)-1,1,1,3,3,3-hexafluoropropane, and 1,6-dihydroxynaphthalene.

Examples of alicyclic epoxy compounds include, but are not limited to, polyglycidyl ethers of polyols having at least one alicyclic ring, or compounds including cyclohexene oxide or cyclopentene oxide obtained by epoxidizing compounds including a cyclohexene ring or cyclopentene ring with an oxidizer. Some particular examples include, but are not limited to, hydrogenated bisphenol A diglycidyl ether; 3,4-epoxycyclohexylmethyl-3,4-epoxycyclohexyl carboxylate; 3,4-epoxy-1-methylcyclohexyl-3,4-epoxy-1-methylhexane carboxylate; 6-methyl-3,4-epoxycyclohexylmethyl-6-methyl-3,4-epoxycyclohexane carboxylate; 3,4-epoxy-3-methylcyclohexylmethyl-3,4-epoxy-3-methylcyclohexane carboxylate; 3,4-epoxy-5-methylcyclohexylmethyl-3,4-epoxy-5-methylcyclohexane carboxylate; bis(3,4-epoxycyclohexylmethyl)adipate; methylene-bis(3,4-epoxycyclohexane); 2,2-bis(3,4-epoxycyclohexyl)propane; dicyclopentadiene diepoxide; ethylene-bis(3,4-epoxycyclohexane carboxylate); dioctyl epoxyhexahydrophthalate; and di-2-ethylhexyl epoxyhexahydrophthalate.

Examples of aliphatic epoxy compounds include, but are not limited to, polyglycidyl ethers of aliphatic polyols or alkylene-oxide adducts thereof, polyglycidyl esters of aliphatic long-chain polybasic acids, homopolymers synthesized by vinyl-polymerizing glycidyl acrylate or glycidyl methacrylate, and copolymers synthesized by vinyl-polymerizing glycidyl acrylate or glycidyl methacrylate and other vinyl monomers. Some particular examples include, but are not limited to glycidyl ethers of polyols, such as 1,4-butanediol diglycidyl ether; 1,6-hexanediol diglycidyl ether; a triglycidyl ether of glycerin; a triglycidyl ether of trimethylol propane; a tetraglycidyl ether of sorbitol; a hexaglycidyl ether of dipentaerythritol; a diglycidyl ether of polyethylene glycol; and a diglycidyl ether of polypropylene glycol; polyglycidyl ethers of polyether polyols obtained by adding one type, or two or more types, of alkylene oxide to aliphatic polyols such as propylene glycol, trimethylol propane, and glycerin; and diglycidyl esters of aliphatic long-chain dibasic acids.

A compound containing one or more polymerizable ethylenically unsaturated group(s) can be a (mono)ethylenically unsaturated monomer or a (poly) ethylenically unsaturated monomer. Examples of compounds containing one or more polymerizable ethylenically unsaturated group(s) include, but are not limited to, those described in U.S. Pat. No. 5,428,125, which is incorporated herein in its entirety by reference.

For one or more embodiments the thermosettable composition includes a solvent. Examples of solvents include, but are not limited to, ketones, amides, alcohols, and esters. Examples of ketones include, but are not limited to, acetone, methyl ethyl ketone, and cyclohexanone. Examples of amides include, but are not limited to, dimethylformamide, dimethylacetamide, and N-methylpyrrolidinone. Examples of alcohols include, but are not limited to, methanol, ethanol, isopropanol, and Dowanol™ PM. Examples of esters include, but are not limited to, methyl acetate, ethyl acetate, and Dowanol™ PMA. The solvent can be 10 weight percent to 75 weight percent of a total weight of the thermosettable composition, where the total weight is based upon the monomers and solvent comprising the thermosettable composition.

For one or more embodiments the thermosettable composition includes an additive. Examples of additives include, but are not limited to, polymerization catalysts, co-curing agents, flame retardants, synergists for flame retardants, solvents, fillers, adhesion promoters, wetting aids, dispersing aids, surface modifiers, thermoplastic resins, and mold release agents, and combinations thereof.

Examples of polymerization catalysts include, but are not limited to, transition metal complexes, imidazoles, phosphonium salts, phosphonium complexes, tertiary amines, hydrazides, "latent catalysts" such as Ancamine 2441 and K61B (modified aliphatic amines available from Air Products and Chemicals, Inc), Ajinomoto Fine-Techno Co., Inc. Ajicure PN-23 or MY-24, modified ureas, and combinations thereof.

Examples of co-curing agents include, but are not limited to, dicyandiamide, substituted guanidines, phenolics, amino compounds, benzoxazine, anhydrides, amidoamines, polyamides, and combinations thereof.

Examples of flame retardants and/or synergists for flame retardants include, but are not limited to, phosphorus containing molecules such as H-DOP (9,10-dihydro-9-oxa-10-phosphaphenanthrene-10-oxide) reaction products, magnesium hydrate, zinc borate, metallocenes, and combinations thereof.

Examples of fillers include, but are not limited to, silica, alumina trihydrate, aluminum oxide, metal oxides, carbon nanotubes, silver flake or powder, carbon black, graphite, and combinations thereof. The filler can be functional and/or non-functional. For various applications, the filler can have a particle size range of from 0.5 nm to 100 μm.

Examples of adhesion promoters include, but are not limited to, modified organosilanes (epoxidized, methacryl, amino, allyl, etc.), acetylacetonates, sulfur containing molecules, titanates, zirconates, and combinations thereof.

Examples of wetting aids and/or dispersing aids include, but are not limited to, modified organosilanes such as, e.g., BYK®-W 900 series and W 9000 series (BYK Additives & Instruments), and modified fluorocarbons.

Examples of surface modifiers include, but are not limited to, slip additives and gloss additives, such as those available from BYK Additives & Instruments.

Examples of thermoplastic resins include, but are not limited to, polyphenylsulfones, polysulfones, polyethersulfones, polyvinylidene fluoride, polyetherimides, polyphthalimides, polybenzimidazoles, acrylics, phenoxy resins, polyurethanes, and combinations thereof. The thermoplastic resin can be reactive and/or non-reactive.

Examples of mold release agents include, but are not limited to, waxes such as, e.g., carnauba wax.

For one or more embodiments, the present disclosure provides a B-staged product that is obtainable by curing the thermosettable composition. The B-staged product can be formed by a process that includes contacting a reinforcement component and a matrix component. The matrix component surrounds and/or supports the reinforcement component. The matrix component and the reinforcement component provide a synergism. This synergism provides that products obtained by curing the B-staged products have mechanical and/or physical properties that are unattainable with only the individual components. For one or more embodiments, the thermosettable compositions, as disclosed herein, are useful as the matrix component.

The reinforcement component can be a fiber. Examples of fibers include, but are not limited to, glass, aramid, carbon, polyester, polyethylene, quartz, metal, ceramic, biomass, and combinations thereof. The fibers can be coated. An example of a fiber coating includes, but is not limited to, boron.

Examples of glass fibers include, but are not limited to, A-glass fibers, E-glass fibers, C-glass fibers, R-glass fibers, S-glass fibers, and T-glass fibers. Aramids are organic polymers, examples of which include, but are not limited to, Kevlar® and Twaron®. Examples of carbon fibers include, but are not limited to, those fibers formed from polyacrylonitrile, pitch, rayon, and cellulose. Examples of metal fibers include, but are not limited to, stainless steel, chromium, nickel, platinum, titanium, copper, aluminum, beryllium, and tungsten. Examples of ceramic fibers include, but are not limited to, those fibers formed from aluminum oxide, silicon dioxide, zirconium dioxide, silicon nitride, silicon carbide, boron carbide, boron nitride, and silicon boride. Examples of biomass fibers include, but are not limited to, those fibers formed from wood and non-wood.

The reinforcement component can be a fabric. The fabric can be formed from the fiber as discussed herein. Examples of fabrics include, but are not limited to, stitched fabrics and woven fabrics. The fabric can be unidirectional or multiaxial. The reinforcement component can be a combination of the fiber and the fabric.

For the B-staged product, the reinforcement component can be exposed to the matrix component via rolling, dipping, spraying, or some other procedure. After the reinforcement component has been exposed to the matrix component a portion of the solvent that is present in the thermosettable composition can be removed via volatilization by heating. The heating can be at a temperature of 90° C. to 200° C., however for some applications the heating can occur at another temperature. While and/or after solvent is removed the matrix component can be partially cured. This partial curing can be referred to as B-staging. The B-staged product can be referred to as a prepreg. B-staging can occur at a temperature of 90° C. to 200° C.; however for some applications the B-staging can occur at another temperature.

The B-staged products can be layered or formed into a shape. For some applications where an electrical laminate is being produced, layers of the B-staged product can be alternated with layers of a conductive material. An example of the conductive material includes, but is not limited to, copper foil. The B-staged product layers can then be exposed to conditions so that the matrix component becomes more fully cured. For example, the B-staged product layers can be exposed to a temperature of 90° C. to 230° C. for a period of time of 10 minutes to 500 minutes. Additionally the B-staged product can be exposed to a pressure of 50 N/cm$^2$ to 500 N/cm$^2$. In this curing process the matrix component on the reinforcement component can flow and mix with the matrix component on adjacent layers thereby fusing the layers together.

The disclosed thermosettable compositions and/or the disclosed B-staged products can be cured to provide products that include, but are not limited to, protective coatings, electrical laminates, structural laminates, composite materials, filament windings, moldings, castings, encapsulations, packagings, and adhesives, among others. Properties of these products can include desirable glass transition temperatures, solvent resistance, moisture resistance, abrasion resistance, and toughness.

EXAMPLES

Materials

KBr, FT-IR grade, ≧99% trace metals basis, available from Sigma-Aldrich.

3-Mercaptopropane-1-sulfonic acid, sodium salt, 90% purity, available from Sigma-Aldrich.

Hydrochloric acid, A.C.S. reagent grade, 37.5% by acid base titration, available from Mallinckrodt Baker, Inc.

Phenol, >99%, available from The Dow Chemical Company.

Allyl alcohol, 99+%, available from Sigma-Aldrich.

Dimethyl carbonate, anhydrous, 99+% available from Sigma-Aldrich

Sodium methoxide, reagent grade, 95%, powder, available from Sigma-Aldrich.

Triphenylphosphine, 99%, available from Sigma-Aldrich.

Palladium-on-carbon, 5% weight on activated carbon, available from Sigma-Aldrich.

Dichloromethane, 99.8%, available from Sigma Aldrich.

4,4'-Isopropylidenediphenol (PARABIS™) available from The Dow Chemical Company. The 4,4'-isopropylidenediphenol assayed 99.72 area % via HPLC analysis with the balance consisting of 2 minor components (0.09 and 0.19 area %, respectively). (PARABIS™ is a Trademark of The Dow Chemical Company ("Dow") or an affiliated company of Dow).

Dicyanate of 4,4'-isopropylidenediphenol was synthesized in the usual manner using 4,4'-isopropylidenediphenol (PARABIS™). HPLC analysis revealed a purity of 100% for the dicyanate recrystallized from acetone. Bisphenol A dicyanate is also available from Huntsman International LLC as AroCy B-10 Monomeric Bisphenol A Dicyanate.

Diatomaceous earth, available as Celite® 545, from Celite Corporation.

Dicyclopentadiene Polyphenol Preparation.

Dicyclopentadiene polyphenol was prepared via condensation of phenol with isomeric dicyclopentadiene dialdehydes (97.3 area %, GC) containing 1.2 area % (GC) mono aldehyde isomers along with some very minor signals attributed to higher molecular weight byproducts. A mole ratio of 20:1 phenol:dicyclopentadiene dialdehyde was employed along with 3-mercapto-1-propane sulfonic acid catalyst at 0.05 mole % with respect to the dicyclopentadiene dialdehyde reactant.

Example 1

Poly(Allyl Ether) of Polycyclopentadiene Polyphenol

Allyl alcohol (50.79 grams, 0.875 moles), dimethyl carbonate (78.78 grams, 0.875 moles) and sodium methoxide catalyst (0.09 gram, 0.065 percent by weight) were added to a 500 milliliter, 3 neck, round bottom glass reactor and maintained at 20° C. while stirred under a nitrogen atmosphere. The reactor included an ambient temperature (22° C.) condenser, a thermometer, both affixed to the reactor via a Claisen adaptor, and an overhead nitrogen inlet, a glass stirring shaft with a Teflon™ stirrer blade coupled to a variable speed motor, and a thermostatically controlled heating mantle. An equilibrium mixture of allylmethyl carbonate, diallyl carbonate and methanol was rapidly formed concurrent with cooling of the reactor contents to 15.3° C. After 18 minutes dicyclopentadiene polyphenol, as described above, (13.32 grams, nominally 0.10 hydroxyl equivalent) was added to the contents of the reactor, which were stirred for 4 minutes to form a solution. Triphenylphosphine (0.28 gram, 0.204 percent by weight) followed by 5% palladium on carbon (0.19 gram, 0.127 percent by weight) were added to the contents of the reactor. Heating commenced and over the next 138 minutes the reaction temperature reached 78° C. The contents of the reactor were maintained at a temperature of 77.0° C. to 79.5° C. for 8 hours and then cooled to 23.5° C. The reactor contents were vacuum filtered through a bed of diatomaceous earth packed on a coarse fritted glass funnel. Dichloromethane was used to remove the product held in the diatomaceous earth. The product was rotary evaporated at a maximum oil bath temperature of 100° C. and to a pressure of 4.1 mm Hg to provide Example 1 (15.70 grams), poly(allyl ether) of polycyclopentadiene polyphenol that was observed to be a transparent, light amber colored, liquid which became a tacky solid at 22° C.

HPLC analysis indicated full conversion of dicyclopentadiene polyphenol to the poly(allyl ether) of dicyclopentadiene polyphenol of Example 1 as indicated by a substantial change in the retention times of all of the individual components. Specifically, under the conditions of the HPLC analysis, the multiple components of the dicyclopentadiene polyphenol reactant were enveloped between retention times of 2.45 and 5.57 minutes while the retention times for the poly(allyl ether) of dicyclopentadiene polyphenol product were enveloped between retention times of 10.22 and 14.84 minutes. Fourier transform infrared (FTIR) spectrophotometric analysis of a film sample of the poly(allyl ether) of dicyclopentadiene polyphenol of Example 1 on a KBr plate provided peaks in the range expected for unsaturated C—H stretch (3029, 3055, 3078 cm$^{-1}$), saturated C—H stretch (2870, 2946 cm$^{-1}$), C=C stretch (1582, 1608 cm$^{-1}$), C—O stretch (1024 cm$^{-1}$), and CH=CH$_2$ deformation (925, 998 cm$^{-1}$), accompanied by total absence of hydroxyl group absorbance thus confirming full conversion of the phenolic hydroxyl groups to allyl ether groups.

Example 2

Thermosettable Composition Including Poly(Allyl Ether) of Polycyclopentadiene Polyphenol The poly(allyl ether) of polycyclopentadiene polyphenol prepared above was used as Example 2, a thermosettable composition of the poly(allyl ether) of polycyclopentadiene polyphenol. Differential scanning calorimetry (DSC) analysis of portions (10.2 and 10.7 milligrams) of Example 2 was performed using a rate of heating of 5° C. per minute from 25° C. to 400° C. under a nitrogen stream (35 cubic centimeters per minute [cc/m]). A pair of exotherms attributed to homopolymerization of the allyl groups were observed with a 211.1° C. onset, 241.9° C. maximum, and a 285.5° C. endpoint accompanied by an enthalpy of 260.2 joules per gram for the initial exotherm and a 288.6° C. onset, 320.1° C. maximum, and a 368.7° C. endpoint accompanied by an enthalpy of 73.6 joules per gram for the second exotherm. Table 1A shows the total cure enthalpy of the thermosettable composition of Example 2.

Example 3

Product Obtained by Curing Thermosettable Composition Including Poly(Allyl Ether) of Polycyclopentadiene Polyphenol Example 3, a homopolymer obtained by curing the poly(allyl ether) of dicyclopentadiene polyphenol of Example 2 that was recovered from the DSC analysis was observed to be a transparent, amber colored, rigid solid.

Synthesis of Bis(Allyl Ether) of 4,4'-Isopropylidenediphenol

Allyl alcohol (101.58 grams, 1.75 moles), dimethyl carbonate (157.55 grams, 1.75 moles) and sodium methoxide catalyst (0.18 gram, 0.065 percent by weight) were added to a 500 milliliter, 3 neck, round bottom glass reactor and maintained at 23° C. while stirred under a nitrogen atmosphere. The reactor included a chilled temperature (0° C.) condenser, a thermometer, magnetic stirring, and a thermostatically controlled heating mantle. An equilibrium mixture of allylmethyl carbonate, diallyl carbonate and methanol was rapidly formed concurrent with cooling of the reactor contents to 15.5° C. After 13 minutes, 4,4'-isopropylidenediphenol (18.33 grams, 0.1606 equivalent of hydroxy groups), was added to the contents of the reactor. Triphenylphosphine (0.56 gram, 0.204 percent by weight) followed by 5% palladium on carbon (0.38 gram, 0.127 percent by weight) were added to the contents of the reactor. The contents of the reactor were heated to 78° C. over 101 minutes, then maintained at that temperature for 8 hours, and then cooled to 22° C. The reactor contents were vacuum filtered through a bed of diatomaceous earth packed on a medium fritted glass funnel. The recovered filtrate was rotary evaporated at a maximum oil bath temperature of 100° C. and to a pressure of 2.9 mm Hg pressure to provide a product (25.21 grams) that was observed to be a transparent, amber colored, liquid at 22° C.

HPLC analysis indicated the presence of bis(allyl ether) of 4,4'-isopropylidenediphenol (95.25 area %) and 12 minor components (ranging from 0.05 to 2.13 area %). The minor components were removed by dissolving the product in dichloromethane (75 milliliters) and passing the resultant solution through a 2 inch deep by 1.75 inch diameter bed of silica gel (230-400 mesh particle size, 60 angstrom mean pore size, 550 m$^2$/gram surface dimension) supported on a medium fritted glass funnel. After elution from the silica gel bed with additional dichloromethane, a yellow band remained in the region of the origin. Rotary evaporation provided bis(allyl ether) of 4,4'-isopropylidenediphenol (23.32 grams, 94.17% isolated yield) that was observed to be a light yellow colored liquid.

HPLC analysis of the chromatographically purified product indicated the presence of bis(allyl ether) of 4,4'-isopropylidenediphenol (99.51 area %) and 3 minor components (0.13, 0.05, and 0.31 area %). FTIR spectrophotometric analysis of a film sample of the bis(allyl ether) of 4,4'-isopropylidenediphenol on a KBr plate provided peaks in the range expected for unsaturated C—H stretch (3039, 3061, 3083 cm$^{-1}$), saturated C—H stretch (2870, 2931 [shoulder present], 2966 cm$^{-1}$), C=C stretch (1581, 1608 cm$^{-1}$), C—O stretch (1025 cm$^{-1}$), and CH=CH$_2$ deformation (926, 998 cm$^{-1}$), and a complete absence of hydroxyl group absorbance indicating full conversion of phenolic hydroxyl groups to allyl ether groups.

Comparative Example A

Thermosettable Composition of Bis(Allyl Ether) of 4,4'-Isopropylidenediphenol The bis(allyl ether) of 4,4'-isopropylidenediphenol prepared above (11.20 milligrams) was used as Comparative Example A, a thermosettable composition of bis(allyl ether) of 4,4'-isopropylidenediphenol. DSC analysis of Comparative Example A was performed with a heating rate of 5° C. per minute from 25° C. to 400° C. under a nitrogen stream (35 cc/m). A pair of exotherms attributed to homopolymerization of the allyl groups were observed with a 201.4° C. onset, 253.4° C. maximum, and a 278.6° C. endpoint accompanied by an enthalpy of 267.1 joules per gram for the initial exotherm and a 278.6° C. onset, 351.2° C. maximum, and a 387.2° C. endpoint accompanied by an enthalpy of 212.2 joules per gram for the second exotherm. Table 1A shows the cure enthalpy of Comparative Example A.

Synthesis of Dicyclopentadiene Polycyanate

Dicyclopentadiene polyphenol, described above, (26.63 grams, nominally 0.20 hydroxyl equivalent) and anhydrous acetone (250 milliliters, 9.39 milliliter per gram of dicyclopentadiene polyphenol) were added to a 500 milliliter, three neck, round bottom glass reactor that was equipped with a chilled condenser (0° C.), a thermometer, an overhead nitrogen inlet (1 liter per minute $N_2$ used), and magnetic stirring. Cyanogen bromide (22.67 grams, 0.0214 mole, 1.07:1 cyanogen bromide:hydroxyl equivalent ratio) was added to the solution in the reactor while maintaining stirring. A dry ice-acetone bath was placed under the reactor and the stirred solution in the reactor was cooled to −6° C. Triethylamine (20.64 grams, 0.0204 mole, 1.02 triethylamine:hydroxyl equivalent ratio) was added to the contents of the reactor, in aliquots using a syringe over 22 minutes so as to maintain a temperature of −8° C. to −3° C. Five minutes later, the light amber colored, transparent solution in the reactor was observed become a light yellow colored slurry that was indicative of a triethylamine hydrobromide co-product formation. After 7 minutes of postreaction at −7° C. to −2° C. HPLC analysis of a sample of the reaction product revealed 24 components with each component present having a different retention time than those observed in the HPLC analysis of the dicyclopentadiene polyphenol reactant. Twenty-seven minutes after the triethylamine addition, during which the reactor contents were maintained at a temperature of −7° C. to −2° C., the reactor contents were added to a beaker containing magnetically stirred deionized water (400 milliliters) and dichloromethane (250 milliliters). The beaker contents were stirred for 2 minutes and then added to a separatory funnel and allowed to separate. The dichloromethane layer was recovered and the aqueous layer was discarded. The dichloromethane layer was added back into the separatory funnel and extracted with fresh deionized water (400 milliliters initially, 250 milliliters thereafter) three additional times to provide a hazy dichloromethane solution. The hazy dichloromethane solution was dried over granular anhydrous sodium sulfate (25 grams) to provide a clear solution that was then passed through a bed of anhydrous sodium sulfate (100 grams) supported on a 400 milliliter, medium flitted glass funnel attached to a side arm vacuum flask. The clear, light yellow colored filtrate thus obtained was rotary evaporated using a maximum oil bath temperature of 55° C. to remove the bulk of the volatiles. Additional rotary evaporation was performed at 75° C. until a vacuum of 0.4 mm Hg was reached, providing a solid powder. The solid powder was then placed in the vacuum oven heated to 75° C. for 16 hours to provide 23.14 grams of dicyclopentadiene polycyanate, which was observed to be a light yellow colored solid. FTIR spectrophotometric analysis of a potassium bromide pellet of the dicyclopentadiene polycyanate demonstrated that there was no hydroxyl group absorbance while a strong cyanate group absorbance at 2265.2 and 2235.4 $cm^{-1}$ was observed. HPLC analysis indicated 16 components with 3 predominant components comprising 27.9, 24.0 and 31.8 area %, respectively.

Comparative Example B

Thermosettable Composition of Dicyclopentadiene Polycyanate

The dicyclopentadiene polycyanate, described above, (6.6 milligrams) was used as Comparative Example B, a thermosettable composition of dicyclopentadiene polycyanate. Differential scanning calorimetry (DSC) analysis of Comparative Example B was performed with a heating rate of 7° C. per minute from 25° C. to 350° C. under a nitrogen stream (35 cc/m). No melt endotherm was detected. A single exotherm attributed to cyclotrimerization was detected with a 162.6° C. onset, a 262.3° C. midpoint, and a 304.6° C. end, accompanied by an enthalpy of 164.4 joules per gram. Table 1B shows the cure enthalpy of the thermosettable composition of Comparative Example B. DSC analysis of the resultant homopolytriazine of dicyclopentadiene polycyanate indicated minor further exothermicity commencing at 271.1° C. A subsequent DSC analysis shifted the onset of minor exothermicity to 307.1° C.

Comparative Example C

Product Obtained by Curing Thermosettable Composition of Dicyclopentadiene Polycyanate The thermosettable composition of Comparative Example B (0.5 gram) was added to an aluminum dish and placed into a 100° C. oven for 1 hour, and then a 150° C. oven for 1 hour. After 23 minutes at 150° C., the dicyclopentadiene polycyanate was a homogeneous liquid. The product was then held in a 200° C. oven for 1 hour, a 250° C. oven for 1 hour and a 300° C. oven for 1 hour followed by cooling to 22° C. to provide Comparative Example C. Comparative Example C was observed to be a transparent, amber colored, rigid solid. DSC analysis of a portion (18.9 milligrams) of Comparative Example C indicated a weak glass transition temperature of 295.7° C., as shown in Table 2A.

Example 4

Thermosettable Composition Including Poly(Allyl Ether) of Polycyclopentadiene Polyphenol (50.0 wt %) and a Comonomer (Dicyclopentadiene Polycyanate, 50.0 wt %)

Poly(allyl ether) of dicyclopentadiene diphenol (0.2064 grams) and dicyclopentadiene polycyanate (0.2064 grams), both described above, were added a glass vial to provide Example 4, a thermosettable composition including poly(allyl ether) of polycyclopentadiene polyphenol and a comonomer (dicyclopentadiene polycyanate). The thermosettable composition of Example 4 was heated to 75° C. while being stirred to provide a solution.

DSC analysis of two portions (10.0 and 10.1 milligrams, respectively) of the thermosettable composition was performed with a heating rate of 5° C. per minute from 25° C. to 400° C. under nitrogen stream (35 cc/m). An exotherm attributed to a copolymerization of the allyl and cyanate groups and any homopolymerization was observed with an average 171.77° C. onset (165.84° C. and 177.69° C.), 229.08° C. maximum (228.46° C. and 229.69° C.), 292.62° C. endpoint (289.54° C. and 295.70° C.), and enthalpy of 253.1 joules per gram (243.0 and 263.1 joules per gram). A second minor exotherm was observed with an average 292.62° C. onset (289.54° C. and 295.70° C.), 322.98° C. maximum (322.78° C. and 323.18° C.), 367.98° C. endpoint (367.74° C. and 368.22° C.), and enthalpy of 20.83 joules per gram (16.32 and 25.34 joules per gram). Table 1B shows the total cure enthalpy of the thermosettable composition of Example 4. Exothermic decomposition was detected commencing at an average temperature of 386.23° C. (386.23° C. and 386.23° C.).

Example 5

Product Obtained by Curing Thermosettable Composition Including Poly(Allyl Ether) of Polycyclopentadiene Polyphenol (50.0 wt %) and a Comonomer (Dicyclopentadiene Polycyanate, 50.0 wt %)

A portion of the thermosettable composition of Example 4 was placed in a 150° C. oven for one hour, a 200° C. oven for one hour, and then a 250° C. oven for one hour to provide Example 5, a product obtained by curing the thermosettable composition of Example 4. DSC analysis of a portion of Example 5 (31.00 milligrams) was performed with a heating rate of 5° C. per minute from 25° C. to 375° C. under nitrogen stream (35 cc/m) and provided residual exothermicity (54.97 joules per gram) at >250° C. associated with completion of the cure. The initial DSC scan of the product of Example 5 indicated a weak glass transition temperature of 300.54° C. with no residual exothermicity. Additional scanning of the same sample indicated a weak glass transition temperature of 302.42° C. Table 2A shows the glass transition temperatures of Example 5, for both DSC analyses. No indication of exothermic decomposition was observed up to the 375° C. DSC analysis temperature in either of the DSC analyses.

Example 6

Thermosettable Composition Including Poly(Allyl Ether) of Polycyclopentadiene Polyphenol (25.0 wt %) and a Comonomer (Dicyanate of 4,4'-Isopropylidenediphenol, 75.0 wt %)

Dicyanate of 4,4'-isopropylidenediphenol (0.5228 grams, 75% wt.) and poly(allyl ether) of dicyclopentadiene diphenol (0.1743 grams, 25% wt.), both described above, were added a glass vial to provide Example 6, a thermosettable composition including poly(allyl ether) of polycyclopentadiene polyphenol and a comonomer (dicyanate of 4,4'-isopropylidenediphenol). The thermosettable composition of Example 6 was heated to 75° C. while being stirred to provide a solution.

DSC analysis of two portions (10.40 and 10.90 milligrams) of the thermosettable composition of Example 6 was performed with a heating rate of 5° C. per minute from 25° C. to 400° C. under nitrogen stream (35 cc/m). An endotherm was observed with an average 57.07° C. onset, 80.63° C. minimum, 87.40° C. endpoint, and enthalpy of 55.52 joules per gram. An exotherm attributed to a copolymerization of the allyl and cyanate groups and any homopolymerization was observed with an average 178.64° C. onset (174.85° C. and 182.43° C.), 242.96° C. maximum (242.62° C. and 243.29° C.), 287.65° C. endpoint (284.80° C. and 290.49° C.), and enthalpy of 517.8 joules per gram (509.4 and 526.2 joules per gram). The copolymer recovered from the DSC analysis was observed to be a transparent, amber colored, rigid solid.

Example 7

Product Obtained by Curing Thermosettable Composition Including Poly(Allyl Ether) of Polycyclopentadiene Polyphenol (25.0 wt %) and Comonomer (Dicyanate of 4,4'-Isopropylidenediphenol, 75.0 wt %)

A portion of the thermosettable composition of Example 6 was cured by placing the portion in a 150° C. oven for one hour, a 200° C. oven for one hour, and then a 250° C. oven for one hour to provide Example 7, a product obtained by curing thermosettable composition of Example 6. DSC analysis of a portion (27.90 milligrams) of the cured product of Example 0.7 was performed with a heating rate of 5° C. per minute from 25° C. to 375° C. under a nitrogen stream (35 cc/m). DCS analysis indicated a glass transition temperature of 247.94° C. with no residual exothermicity noted. No indication of exothermic decomposition was observed up to the 375° C. DSC analysis temperature. Table 2B shows the cured product of Example 7, glass transition temperature and onset to exothermic decomposition.

Thermogravimetric Analysis (TGA) of DSC analyzed cured product (27.49 milligrams), described above, was conducted using a rate of heating of 10° C. per minute from 25° C. to 600° C. under a dynamic nitrogen atmosphere. A step transition with an onset temperature of 418.90° C. and an end temperature of 455.74° C. was observed. The following weight % residue was recorded at the indicated temperature: 100%-100° C., 100%-200° C., 99.99%-300° C., 99.96%-325° C., 99.88%-350° C., 99.61%-375° C., 98.85%-400° C., 90.63%-425° C. Tables 3A and 3B summarize the TGA data.

Comparative Example D

Thermosettable Composition Including Bis(Allyl Ether) of 4,4'-Isopropylidenediphenol (25.0 wt %) and Dicyanate of 4,4'-Isopropylidenediphenol (75.0 wt %)

Dicyanate of 4,4'-isopropylidenediphenol (2.5518 grams, 75% wt.) and bis(allyl ether) of 4,4'-isopropylidenediphenol (0.8506 grams, 25% wt.), both described above, were added to a glass vial to provide the thermosettable composition of Comparative Example D. The thermosettable composition was heated to 75° C. while being stirred to provide a solution. DSC analysis of two portions (11.40 and 12.80 milligrams, respectively) of the thermosettable composition was performed with a heating rate of 5° C. per minute from 25° C. to 400° C. under nitrogen stream (35 cc/m). An endotherm was observed with an average 31.00° C. onset (30.29° C. and 31.71° C.), 71.48° C. minimum (71.35° C. and 71.61° C.), 79.82° C. endpoint (78.63° C. and 81.00° C.), and enthalpy of 64.6 joules per gram (62.10 and 67.01 joules per gram). An exotherm attributed to a copolymerization of the allyl and cyanate groups and any homopolymerization was observed with an average 195.70° C. onset (194.75° C. and 196.65° C.), 256.11° C. maximum (255.56° C. and 256.65° C.), 286.94° C. endpoint (285.75° C. and 288.12° C.), and enthalpy of 769.3 joules per gram (757.9 and 780.7 joules per gram). Table 1C shows the cure enthalpy of the thermosettable composition of Comparative Example D. The copolymer recovered from the DSC analysis was observed to be a transparent, amber colored, rigid solid.

Comparative Example E

Product Obtained by Curing Thermosettable Composition Including Bis(Allyl Ether) of 4,4'-Isopropylidenediphenol (25.0 wt %) and Dicyanate of 4,4'-Isopropylidenediphenol (75.0 wt %)

A portion of the thermosettable composition of Comparative Example D was cured by placing in a 150° C. oven for one hour, a 200° C. oven for one hour, and then a 250° C. oven for one hour to provide Comparative Example E, a product obtained by curing the thermosettable composition of Comparative Example D. DSC analysis of two portions of the cured product of Comparative Example E (30.4 and 30.8 milligrams) indicated residual exothermicity at >200° C. After a second scanning an average glass transition temperature of 162.47° C. (158.70° C. and 166.23° C.) was measured with residual exothermicity followed by exothermic decomposition commencing at an average temperature of 354.2° C. (351.6° C. and 356.8° C.) (individual values in parenthesis). Table 2B shows the cured product of Comparative Example E, glass transition temperature and onset to exothermic decomposition.

TGA of DSC analyzed cured product (28.60 milligrams), described above, was conducted using a rate of heating of 10° C. per minute from 25° C. to 600° C. under a dynamic nitrogen atmosphere A step transition with an onset temperature of 386.65° C. and an end temperature of 428.52° C. was observed. The following weight % residue was recorded at the indicated temperature: 100%-100° C., 100.0%-200° C., 99.91%-300° C., 99.64%-325° C., 98.97%-350° C., 97.05%-375° C., 82.23%-400° C., 56.46%-425° C. Tables 3A and 3B summarize the TGA data.

TABLE 1A

| Example/Comparative Example | Cure Enthalpy (joules/gram) |
|---|---|
| Example 2 | 334 |
| Comparative Example A | 479 |

The data in Table 1A shows that Example 2, the thermosettable composition including poly(allyl ether)s of polycyclopentadiene polyphenol, has a lower cure enthalpy than Comparative Example A, the composition including bis(allyl ethers) of 4,4'-isopropylidene diphenol.

TABLE 1B

| Example/Comparative Example | Cure Enthalpy (joules/gram) |
|---|---|
| Example 4 | 274 |
| Comparative Example B | 164 |

The data in Table 1B shows that Example 4, the thermosettable composition including poly(allyl ether)s of polycyclopentadiene polyphenol (50.0 wt %) and the comonomer dicyclopentadiene polycyanate (50.0 wt %), has a higher cure enthalpy than Comparative Example B, the composition including only dicyclopentadiene polycyanate. However, persistent residual exothermicity associated with curing was observed in the thermosettable composition of Comparative Example B thus the 164 joules/gram cure enthalpy is artificially low and does not include the full amount of energy associated with complete cure. In contrast, there was no residual exothermicity associated with curing of the thermosettable composition of Example 4.

TABLE 1C

| Example/Comparative Example | Cure Enthalpy (joules/gram) |
|---|---|
| Example 6 | 518 |
| Comparative Example D | 769 |

The data in Table 1C shows that Example 6, the thermosettable composition including poly(allyl ether) of polycyclopentadiene polyphenol (25.0 wt and the comonomer dicyanate of 4,4'-isopropylidenediphenol (75.0 wt %), has a lower cure enthalpy than Comparative Example D, the composition including bis(allyl ether) of 4,4'-isopropylidenediphenol (25.0 wt %) and dicyanate of 4,4'-isopropylidenediphenol (75.0 wt %).

TABLE 2A

| Example/Comparative Example | Glass Transition Temperature (° C.) |
|---|---|
| Example 5 (first scan) | 301 |
| Example 5 (second scan) | 302 |
| Comparative Example C | 296 |

The data in Table 2A shows that Example 5, first scan and second scan, the cured product obtained by curing the thermosettable composition of Example 4, has a greater glass transition temperature than Comparative Example C, the product obtained by curing the thermosettable composition of Comparative Example B. Additionally, for the cured product of Example 5, high thermal stability is indicated by the ability to undergo a second DSC scan without any decrease in glass transition temperature.

TABLE 2B

| Example/Comparative Example | Glass Transition Temperature (° C.) | Exothermic Decomposition Onset Temperature (° C.) |
|---|---|---|
| Example 7 | 248 | >375 |
| Comparative Example E | 163 | 354 |

The data in Table 2B shows that the cured product of Example 7, the product obtained by curing the thermosettable composition of Example 6, has a greater glass transition temperature than that of the cured product of Comparative Example E, the product obtained by curing the thermosettable composition of Comparative Example D. Additionally, higher thermal stability of the cured product of Example 7 is indicated relative to the cured product of Comparative Example E.

TABLE 3A

| Example/Comparative Example | Residue (weight %) | | | | | | |
| --- | --- | --- | --- | --- | --- | --- | --- |
| | 100° C. | 200° C. | 300° C. | 325° C. | 350° C. | 375° C. | 400° C. | 425° C. |
| Example 7 (Thermogravimetric Analysis) | 100 | 100 | 99.99 | 99.96 | 99.88 | 99.61 | 98.85 | 90.63 |
| Comparative Example E (Thermogravimetric Analysis) | 100 | 100 | 99.91 | 99.64 | 98.97 | 97.05 | 82.23 | 56.46 |

TABLE 3B

| Example/Comparative Example | Step Transition Onset Temperature (° C.) | Step Transition End Temperature (° C.) |
| --- | --- | --- |
| Example 7 (Thermogravimetric Analysis) | 419 | 456 |
| Comparative Example E (Thermogravimetric Analysis) | 387 | 429 |

The data of Tables 3A and 3B indicate higher thermal stability for the cured product of Example 7 (Thermogravimetric Analysis) relative to the cured product of Comparative Example E (Thermogravimetric Analysis).

What is claimed:

1. A poly(allyl ether) of polycyclopentadiene polyphenol of Formula I:

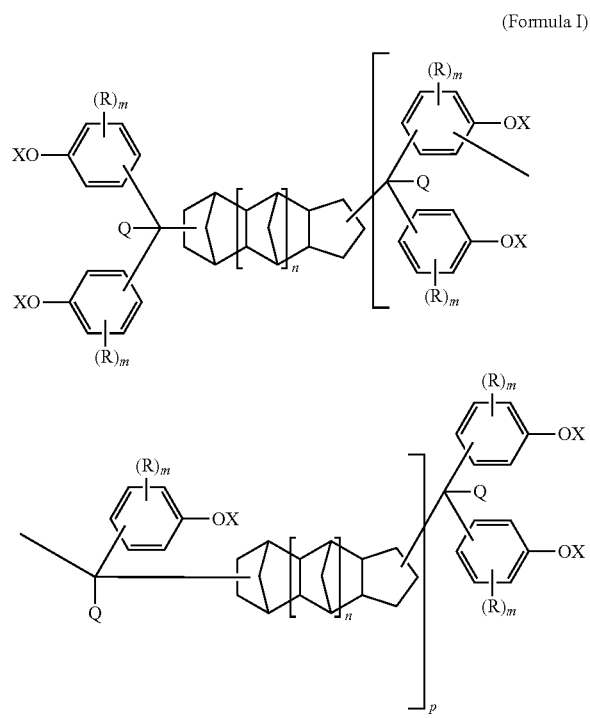

(Formula I)

in which each n independently has a value from zero to 20; each m independently has a value of zero to 3; p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to 6 carbon atoms; each Q is independently hydrogen or an alkyl group containing 1 to 6 carbon atoms; and each X is independently selected from the group consisting of hydrogen, $HR^1C=CR^1-CH_2$, and $H_2R^1C-CR^1=HC$, where each $R^1$ is independently selected from the group consisting of hydrogen and substituted alkyl groups having from 1 to 3 carbon atoms, with the proviso that when each X is hydrogen then at least one R group is selected from the group consisting of $HR^1C=CR^1-CH_2$ and $H_2R^1C-CR^1=HC$.

2. The poly(allyl ether) of polycyclopentadiene polyphenol of claim 1, wherein each R is a halogen independently selected from the group of fluorine, chlorine, and bromine.

3. The poly(allyl ether) of polycyclopentadiene polyphenol of claim 1, wherein each n independently has a value from zero to 8.

4. The poly(allyl ether) of polycyclopentadiene polyphenol of claim 1, wherein p has a value from zero to 1.

5. The poly(allyl ether) of polycyclopentadiene polyphenol of claim 1, wherein each alkyl group independently contains 1 to 2 carbon atoms.

6. The poly(allyl ether) of polycyclopentadiene polyphenol of claim 1, wherein each alkoxy group independently contains 1 to 2 carbon atoms.

7. The poly(allyl ether) of polycyclopentadiene polyphenol of claim 1, wherein the alkyl group is substituted with a halogen selected from the group consisting of chlorine and bromine.

8. The poly(allyl ether) of polycyclopentadiene polyphenol of claim 1, wherein the alkoxy group is substituted with a halogen selected from the group consisting of chlorine and bromine.

9. The poly(allyl ether) of polycyclopentadiene polyphenol of claim 1, wherein m is zero.

10. A thermosettable composition comprising the poly(allyl ether) of polycyclopentadiene polyphenol of claim 1.

11. The thermosettable composition of claim 10, further comprising a comonomer selected from the group consisting of polymaleimides, polycyanates, polycyanamides, epoxy compounds, allyl compounds, compounds containing one or more polymerizable ethylenically unsaturated group(s), and combinations thereof.

12. The thermosettable composition of claim 11, wherein the comonomer is from 5 weight percent to 90 weight percent of a total weight percent the monomers included in the thermosettable composition.

13. A product obtainable by curing the thermosettable composition of claim 10.

14. The product as in claim 13, where the product comprises a B-staged product.

15. The product of claim 13, where the product comprises an infusible polymer network.

* * * * *